United States Patent [19]

Heller et al.

[11] Patent Number: 4,946,931
[45] Date of Patent: Aug. 7, 1990

[54] POLYMERS CONTAINING CARBOXY-ORTHO ESTER AND ORTHO ESTER LINKAGES

[75] Inventors: Jorge Heller, Woodside; Steve Y. W. Ng, San Francisco; Donald W. H. Penhale, Menlo Park, all of Calif.

[73] Assignee: Pharmaceutical Delivery Systems, Inc., Menlo Park, Calif.

[21] Appl. No.: 366,125

[22] Filed: Jun. 14, 1989

[51] Int. Cl.$^5$ .................................................. C08G 2/00
[52] U.S. Cl. ..................................... 528/230; 528/220; 528/222; 528/232; 528/271; 528/274; 528/300; 528/302; 528/308; 528/308.6; 528/403; 528/406; 528/392; 514/866; 514/950; 514/964; 424/78; 424/426; 523/105
[58] Field of Search ............... 528/220, 222, 230, 232, 528/271, 274, 300, 302, 308, 308.6, 403, 406, 392; 514/866, 950, 964; 424/78, 426; 523/105

[56] References Cited

U.S. PATENT DOCUMENTS

| | | | |
|---|---|---|---|
| 4,131,648 | 12/1978 | Choi et al. | 424/22 |
| 4,180,646 | 12/1979 | Choi et al. | 528/153 |
| 4,304,767 | 12/1981 | Heller et al. | 424/78 |
| 4,513,143 | 4/1985 | Ng et al. | 549/335 |
| 4,532,335 | 7/1985 | Helwing | 549/335 |
| 4,675,189 | 6/1987 | Kent et al. | 424/490 |
| 4,764,364 | 8/1988 | Heller et al. | 424/78 |
| 4,855,132 | 8/1989 | Heller et al. | 424/78 |

*Primary Examiner*—John Kight, III
*Assistant Examiner*—Sam A. Acquah
*Attorney, Agent, or Firm*—Irell & Manella

[57] ABSTRACT

Polymers are provided that are useful for making biodegradable sustained release agent dispensers and which contain at least one of the following mer units (I) and (II)

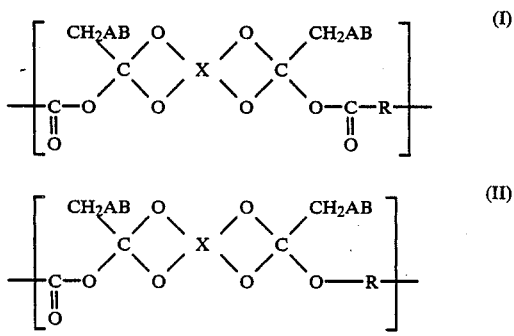

wherein X is a quadrivalent organic grouping, A and B are hydrogen or lower alkyl, and R is hydrocarbyl or oxyhydrocarbyl of 1 to 14 carbon atoms and, if oxyhydrocarbyl, containing 1 to 4 oxy groups, and may be either aliphatic or aryl, unsubstituted or substituted with one or more lower alkyl, amino, nitro or halogen moieties. Methods of synthesizing the novel polymers are also provided, as biodegradable beneficial agent dispensers prepared using the novel polymers.

18 Claims, 2 Drawing Sheets

POLYMERS CONTAINING CARBOXY-ORTHO ESTER AND ORTHO ESTER LINKAGES

DESCRIPTION

1. Technical Field

The invention is in the field of bioerodible polymers, and relates generally to novel polymers having carboxy-ortho ester as well as ortho ester linkages. The invention also relates to bioerodible or biodegradable devices fabricated from the novel polymers and which are useful for dispensing beneficial agents.

2. Background Art

Interest in synthetic biodegradable polymers for the systemic delivery of therapeutic agents began in the early 1970' s with the work of Yolles et al. on poly(lactic acid), poly(glycolic acid) and copolymers thereof. Since that time various other polymers have been made or investigated for such use.

U.S. Pat. Nos. 4,093,709, 4,131,648, 4,138,344 and 4,180,646 describe biodegradable or bioerodible poly (ortho ester) polymers. These polymers are the reaction product of an ortho ester (or an ortho carbonate) such as 2,2-diethoxytetrahydrofuran with a diol such as 1,4-cyclohexanedicarbinol. The reaction must be carried out at elevated temperature, under reduced pressure and requires a relatively long reaction time. Drug or other active agent is dispersed in the polymer and is released therefrom as the polymer biodegrades due to hydrolysis of the labile linkages.

U.S. Pat. No. 4,304,767 describes another type of poly (ortho ester) which is made by reacting a polyol with a polyfunctional ketene acetal. However, because ortho ester linkages at body pH and temperature are relatively stable, their hydrolysis rate is slow and thus the release of therapeutic agents dispersed in the polymer is also slow. Therefore, to achieve therapeutically useful drug delivery rates, the hydrolysis of the polymer must be catalyzed by the addition of acidic excipients.

The polymers of the present invention are also prepared from a polyfunctional ketene acetal but provide carboxy-ortho ester linkages as well as ortho ester linkages between the various mer units. Introduction of carboxy-ortho ester groups between the various mer units provides a means for controlling the rate at which the polymer biodegrades and, therefore, the addition of acidic compounds to catalyze polymer hydrolysis is not necessary. This is a significant advantage. We have also found that the rate of hydrolysis of the novel carboxy-ortho ester linkage is much faster than the rate of hydrolysis of an ortho ester linkage, and that controlling the relative amounts of these two types of linkages between the various mer units also enables control over the rate at which the polymer biodegrades.

It is not possible to make the present polymers by the method described in U.S. Pat. No. 4,304,767, i.e., by reacting a polyol with a polyfunctional ketene acetal. In this regard, the present polymers are made by reacting a polyfunctional ketene acetal with polyfunctional carboxylic acids or monomers having one hydroxy and one or more carboxy groups.

A further substantial difference between polymers described in the present invention and those described in the '767 patent is that the present reaction between carboxylic acid groups and ketene acetals occurs spontaneously and thus requires no acid catalyst.

DISCLOSURE OF THE INVENTION

The present invention provides novel bioerodible polymers, a process for making those polymers, and bioerodible devices fabricated from the novel polymers which are useful for delivering beneficial agents.

The polymers of the invention are characterized by containing at least one of the mer units given by formulae (I) or (II)

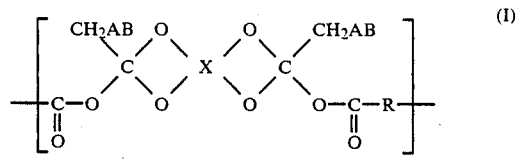

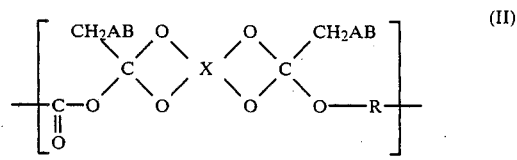

wherein X is a quadrivalent organic grouping, A and B are hydrogen or lower alkyl and may be the same or different, and R is an alkyl, cycloalkyl or aryl moiety as will be described.

The process for making these polymers comprises reacting a diketene acetal of formula (IIIa) or (IIIb)

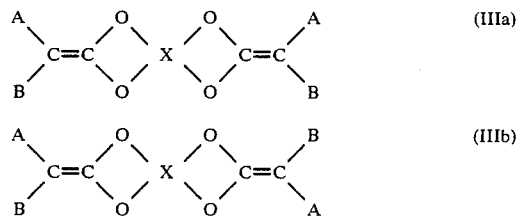

where X, A and B are as given above, with a hydroxycarboxylic acid or a dicarboxylic acid of formulae (IV) or (V), respectively.

The bioerodible devices of the invention comprise bodies of the novel polymer admixed with a beneficial agent or coated into a beneficial agent composition.

MODES FOR CARRYING OUT THE INVENTION

Figure 1:
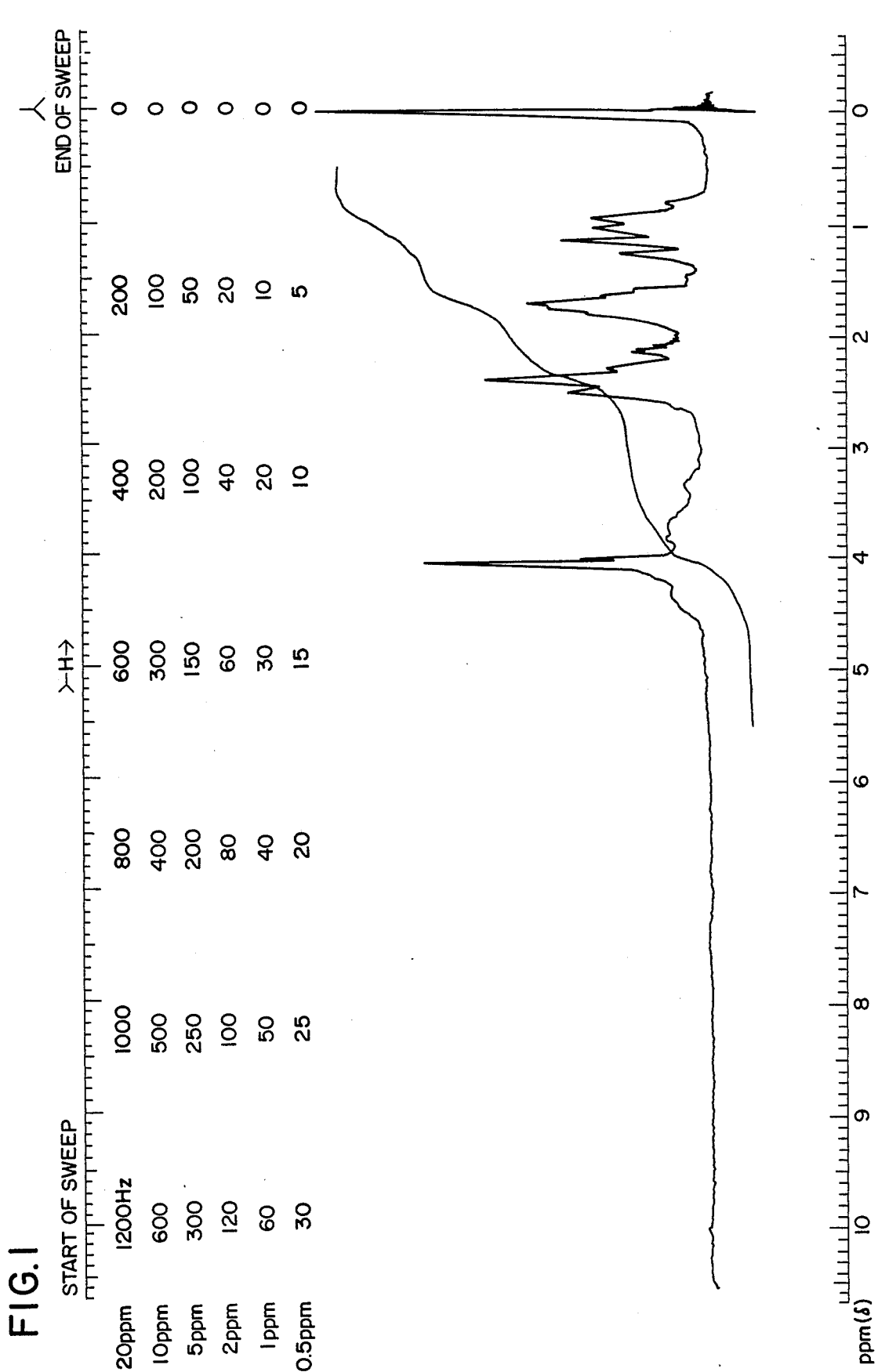
FIGS. 1 and 2 are NMR spectra of the polymers obtained in Examples 1 and 2, respectively.

The term "mer" intends the structurally recurring units or monomer units of the polymers of the invention. The mers of a given polymer may be the same or different, and when different, may be arranged in block or random fashion. When the mers of a polymer are the same, the polymer is called a homopolymer; when they are different, the polymer is called a copolymer.

The terms "biodegradable" and "bioerodible", as used herein to describe the novel polymers, intend solid, gel or viscous polymers that completely solubilize as a consequence of hydrolysis.

The term "beneficial agent" as used herein intends a compound or composition of matter that provides a desired and useful effect upon the environment or individual (man or animal) to which it is administered. This term includes, without limitation, agents such as drugs, nutrients, plant growth regulants, pesticides, catalysts, disinfectants, and the like.

The term "drug" as used herein intends a compound or composition of matter which when administered to an individual (man or animal) induces a desired pharmacologic and/or physiologic effect by local and/or systemic action. In general, the term includes the therapeutic or prophylactic agents in all major therapeutic/prophylactic areas of medicine.

The term "effective amount" as used herein intends that quantity of agent that is required to provide the desired or intended beneficial effect without intolerable side effects, such as toxicity.

"Lower alkyl" as used herein is intended to mean a linear or branched alkyl substituent having 1 to 6 carbon atoms.

The X grouping in formulae (I), (II), (IIIa) and (IIIb) is a quadrivalent organic moiety which may be, for example, a tetravalent carbon atom, a neopentyl group, a tetra-substituted cyclohexyl species, or the like. A and B, as noted, are independently selected from the group consisting of hydrogen and lower alkyl.

The symbol R in the formulae represents a hydrocarbyl or oxyhydrocarbyl group of 1 to 14 carbon atoms, usually 2 to 9 carbon atoms. The number of oxy (—O—) groups in the oxyhydrocarbyl moiety will typically be 1 to 4. The hydrocarbyl group will preferably be saturated, branched- or straight-chain aliphatic or saturated cycloaliphatic, unsubstituted or substituted with one or more moieties which will not interfere with the polymerization reaction, e.g., lower alkyl, amino, nitro, halogen, or the like.

The R moieties may also be aryl, in which case they are preferably carbocyclic, and may be monocyclic or polycyclic (fuse) of 2 to 4 rings, but will typically contain 1 or 2 rings, which may be unsubstituted or substituted as described above.

The number of repeating mer units in the polymer will normally be in the range of 2 to 1000, preferably 2 to 200, and most preferably 5 to 200.

Example of suitable diketene acetal monomers are to given in Table I.

TABLE I

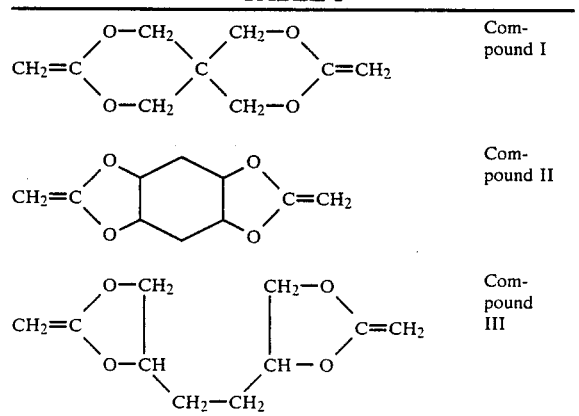

TABLE I-continued

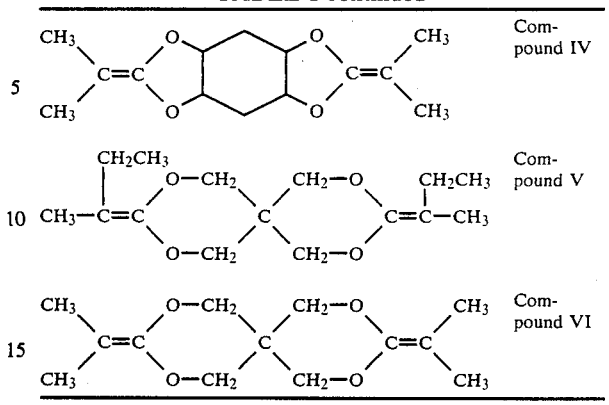

The carboxylic acid reactant, as noted, is either a dicarboxylic acid or a hydroxy-carboxylic acid reactant, given by either HOOC—R—COOH or HOOC—R—OH, respectively (with R as defined previously), and thus contains either (i) two carboxylic acid groups or (ii) one carboxylic acid group and one hydroxyl moiety. In either case, the two functional groups may be on the terminal carbon atoms of aliphatic chains or are para with respect to each other in six-membered carbocyclic groups, or are terminal in linear polyesters or polyethers. Examples of carboxylic acid reactants include adipic acid, sebatic acid, p-hydroxybenzoic acid, terephthalic acid, cyclohexane dicarboxylic acid, glycolic acid and lactic acid. If desired, both a dicarboxylic acid and a hydroxycarboxylic acid may be used, i.e., to react simultaneously with the diketene acetal.

The polymers are made via a condensation reaction between the diketene acetal and the dicarboxylic acid or the hydroxy-carboxylic acid reactant. No catalyst is required. The process may be carried out neat (no solvent) or in aprotic solvents such as tetrahydrofuran (THF), glyme (ethylene glycol dimethyl ether), diglyme, cymene, cumene, or chlorinated hydrocarbons. In either case, care should be taken to maintain anhydrous conditions. The reaction will normally be run at temperatures in the range of 20° to 150° C., preferably 20° to 75° C. The preferred approximate mol ratio of reactants (diketene acetal: dicarboxylic or hydroxy-carboxylic acid) is in the range of about 3:2 to 2:3, and a particularly preferred mol ratio is approximately 1:1. While this ratio may be altered, significant variation is not desirable as the molecular weight range of the product is dependent on the mol ratios of the reactants. The exact range of each reactant which will provide the desired product is dependent upon the purity and volatility of the reactant.

The following examples further illustrate the ortho ester polymers of the invention and the process by which they may be prepared. These examples are not intended to limit the invention in any manner.

EXAMPLE 1

Under anhydrous conditions 10.61 g (0.05 mole) of 3,9-bis(ethylene)2,4,8,10-tetraoxaspiro[5,5]undecane (DETOSU) and 7.31 g (0.05 mole) of adipic acid were weighed into a 100 ml round bottom flask. The mixture was dissolved in 20 ml of dry, distilled tetrahydrofuran. Polymerization started spontaneously, the solution warmed to about 50° C. and the temperature gradually returned to room temperature. After stirring at room temperature for minutes, 1 ml of triethylamine was added as a stabilizer and the solution evaporated to dryness. A solid polymer was obtained. The polymer is highly susceptible to hydrolytic degradation so that extreme care was taken to avoid exposure to moisture.

The following polymer was obtained:

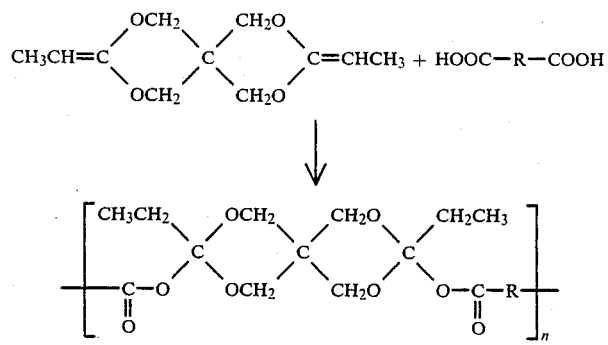

In this particular example, R had the following structure: —(CH$_2$)$_6$—.

The structure of the product was confirmed by $^1$H NMR spectroscopy (the NMR spectrum is shown in FIG. 1). The mole average molecular weight was determined by gel permeation chromatography (GPC) analysis to be approximately 15,000.

EXAMPLE 2

Following a procedure identical to that was allowed to react with 6.91 g (0.05 mole) of p-hydroxybenzoic acid (Aldrich) to obtain a polymer having the following structure:

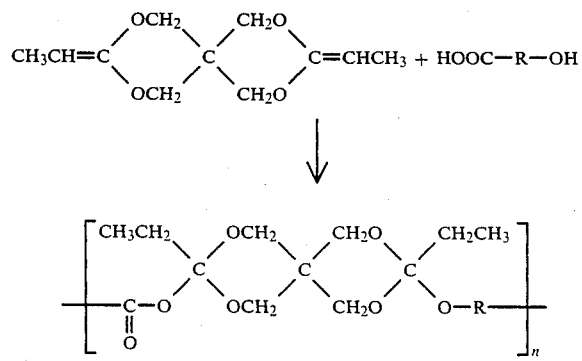

In this particular example, R had the following structure:

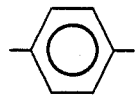

Figure 2:
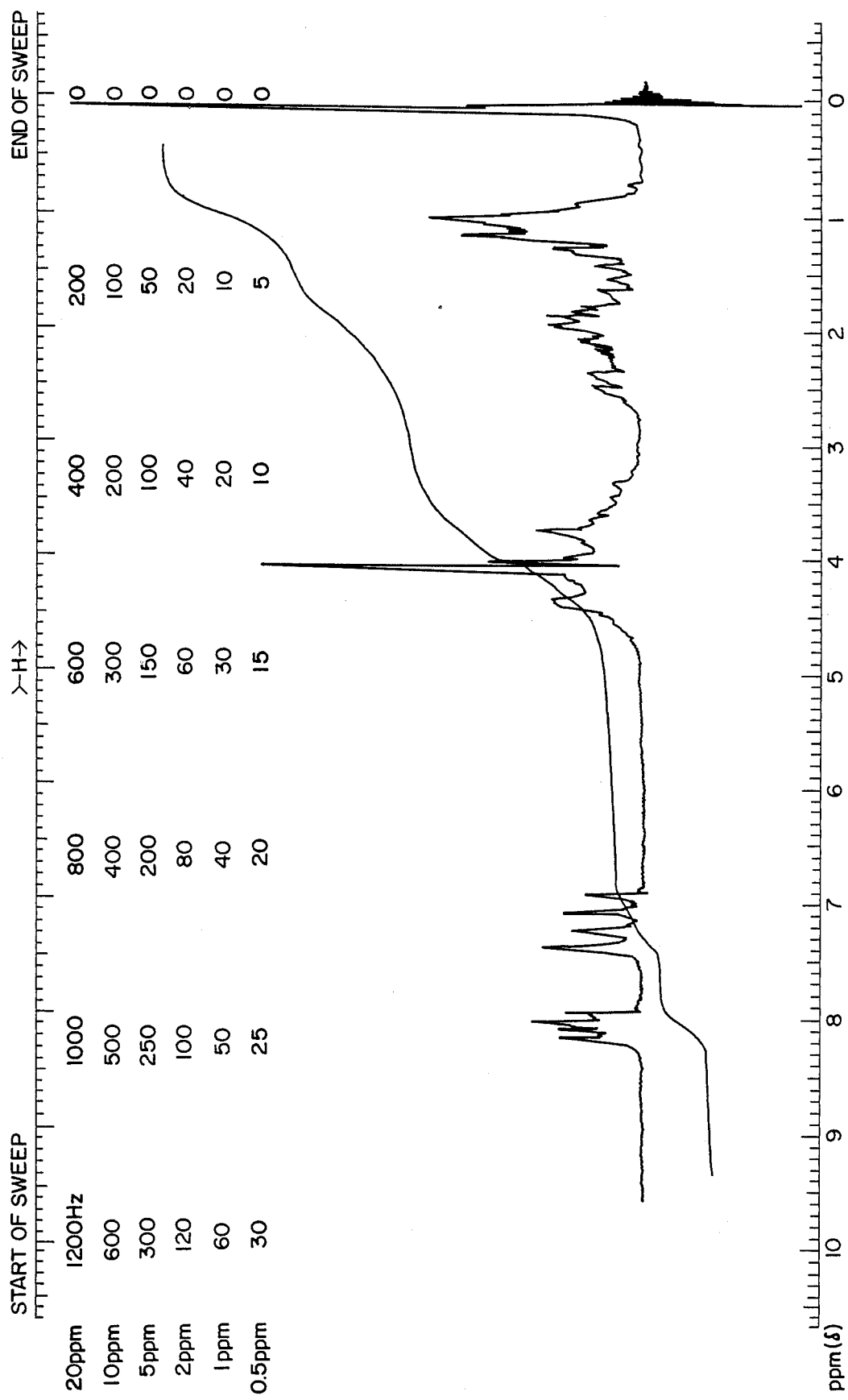

The structure of the product was confirmed by $^1$H NMR spectroscopy (the NMR spectrum is shown in FIG. 2). The mole average molecular weight was determined by GPC analysis to be approximately 21,000.

EXAMPLE 3

Following a procedure identical to that described under Example 1, 10.61 g (0.05 mole) of DETOSU is reacted with 8.31 g (0.05 mole) of terephthalic acid (Aldrich) to obtain a polymer having the structure shown in Example 1. In this particular case R has the following structure:

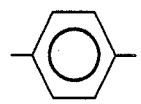

EXAMPLE 4

Following a procedure identical to that described under Example 1, 10.61 g (0.05 mole) of DETOSU is reacted with 8.61 g (0.05 mole) of cyclohexane dicarboxylic acid (Aldrich) to obtain a polymer having the structure shown in Example 1. In this particular case R has the following structure:

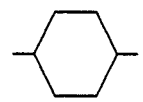

EXAMPLE 5

Following a procedure identical to that described under Example 1, 10.61 g (0.05 mole) of DETOSU is reacted with 10.12 g (0.05 mole) of sebatic acid (Aldrich) to obtain a polymer having the structure shown in Example 1. In this particular case R has the following structure: —(CH$_2$)$_8$—.

EXAMPLE 6

Following a procedure identical to that described under Example 1, 10.61 g (0.05 mole) of DETOSU is reacted with 3.81 g (0.05 mole) of glycolic acid (Aldrich) to obtain a polymer having the structure shown in Example 2. In this particular case R has the following structure: —(CH₂)—.

EXAMPLE 7

Following a procedure identical to that described under Example 1, 10.61 g (0.05 mole) of DETOSU is reacted with 4.51 g (0.05 mole) of lactic acid (Aldrich) to obtain a polymer having the structure shown in Example 2. In this particular case R has the following structure: —CH(CH₃)—.

EXAMPLE 8

Following a procedure identical to that described under Example 1, 10.61 g (0.05 mole) of DETOSU is reacted with 2.2 g (0.025 mole) of lactic acid and 3.6 g (0.025 mole) of adipic acid to obtain a polymer having a structure similar to that shown in Example 2. In this particular case the R moieties are —CH(CH₃)— and —(CH₂)₄—.

The devices of the invention for dispensing beneficial agents may be made by mixing (dispersing) the beneficial agent (e.g., drug) with the polymer to form a homogeneous dispersion of polymer and agent and forming the dispersion into the desired shape or by coating a body of beneficial agent composition with the polymer. Both of these techniques of making biodegradable sustained-release devices have been described with respect to other orthoester polymers (see, for instance, U.S. Pat. No. 4,093,709) and thus do not need to be reiterated.

Modification of the above-described modes for carrying out the invention that are obvious to those of skill in the fields of polymer chemistry and sustained release dispensers are intended to be within the scope of the following claims.

We claim:

1. A polymer containing at least one of the following mer units (I) and (II)

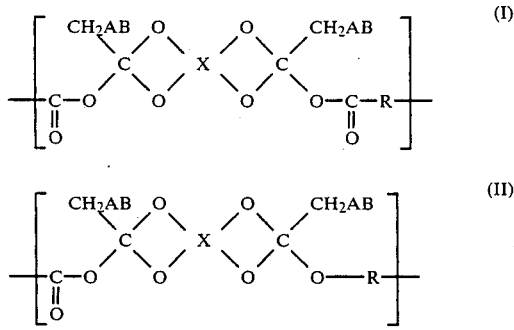

wherein X is a quadrivalent organic grouping, A and B are independently selected from the group consisting of hydrogen and lower alkyl, and R is hydrocarbyl or containing 1 to 4 oxy groups, and may be either aliphatic or aryl, unsubstituted of substituted with one or more lower alkyl, amino, nitro or halogen moieties.

2. The polymer of claim 1, wherein R is hydrocarbyl of 2-9 carbon atoms.
3. The polymer of claim 1, wherein X is a tetravalent carbon atom.
4. The polymer of claim 1, wherein X is neopentyl.
5. The polymer of claim 1, wherein X is cyclohexyl.
6. The polymer of claim 1, wherein R is phenyl.
7. The polymer of claim 1, wherein R is cyclohexyl.
8. The polymer of claim 1, wherein R is lower alkyl.
9. The polymer of claim 1, wherein the number of mer units in the polymer is in the range of 5 to 200.
10. A method for preparing the polymer of claim 1, comprising reacting a diketene acetal with a carboxylic acid reactant selected from the group consisting of a dicarboxylic acid, a hydroxy-carboxylic acid, or mixtures thereof, under anhydrous conditions.
11. The method of claim 10, wherein the diketene acetal is given by the structure

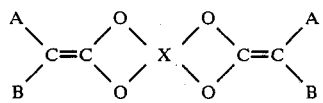

or

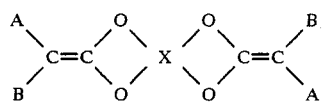

12. The method of claim 10, wherein the carboxylic acid reactant is given by HOOC—R—OH or HOOC—R—COOH, wherein R is a quadrivalent organic grouping, A and B are independently selected from the group consisting of hydrogen and lower alkyl, and R is hydrocarbyl or oxyhydrocarbyl of 1 to 14 carbon atoms and, if oxyhydrocarbyl, containing 1 to 4 oxy groups, and may be either aliphatic or aryl, unsubstituted or substituted with one or more lower alkyl, amino, nitro or halogen moieties.
13. The method of claim 10, wherein the reaction is carried out in an aprotic solvent.
14. The method of claim 10, wherein the reaction is carried out neat.
15. The method of claim 10, wherein the approximate mol ratio of diketene acetal to the carboxylic acid reactant is about 3:2 to 2:3.
16. The method of claim 10, wherein the approximate mol ratio of diketene acetal to the carboxylic acid reactant is about 1:1.
17. A biodegradable beneficial agent dispenser comprising a body comprised of a dispersion of a beneficial agent in the polymer of claim 1.
18. A biodegradable beneficial agent dispenser comprising a body of a beneficial agent composition coated with the polymer of claim 1.

* * * * *